United States Patent
Portetelle et al.

(12)

(10) Patent No.: US 6,455,049 B1
(45) Date of Patent: Sep. 24, 2002

(54) BIOLOGICALLY ACTIVE AND PARTICULARLY PEPTIDE MOLECULES HAVING A POTENTIATING EFFECT ON GROWTH HORMONE BIOLOGICAL ACTIVITY

(76) Inventors: Daniel Portetelle, 11 rue de la Motte, B-5881 Meux-la-Bruyere (BE); Robert Renaville, 18 rue de Moha, B-5030 Gembloux (BE)

( * ) Notice: Subject to any disclaimer, the term of this patent is extended or adjusted under 35 U.S.C. 154(b) by 0 days.

(21) Appl. No.: 09/101,912

(22) PCT Filed: Jan. 22, 1997

(86) PCT No.: PCT/FR97/00127

§ 371 (c)(1), (2), (4) Date: Dec. 4, 1998

(87) PCT Pub. No.: WO97/27298

PCT Pub. Date: Jul. 31, 1997

(30) Foreign Application Priority Data

Jan. 26, 1996 (FR) .............................................. 96 00956

(51) Int. Cl.[7] ........................ A61K 39/00; A61K 38/00; C07K 5/00; C07H 21/04
(52) U.S. Cl. ................................ 424/198.1; 424/178.1; 530/300; 530/328; 530/350; 530/399; 530/388.22; 536/23.5; 514/2
(58) Field of Search .................................. 530/300, 350, 530/399, 388.22, 328, 402; 424/178.1, 198.1; 536/23.5; 514/2

(56) References Cited

U.S. PATENT DOCUMENTS 5,143,726 A * 9/1992 Thornton ..................... 424/88

FOREIGN PATENT DOCUMENTS

| EP | 303 488 | 2/1989 |
| EP | 0303488 A2 * | 7/1989 |
| WO | WO 94 05697 | 3/1994 |

OTHER PUBLICATIONS

Aston et al. Mol. Immun. 28:42–50, 1991.*
Bowie et al., Science 247(1306–1310) 1990.*
Wells Biochemistry 29(8509–8517) 1990.*
Ngo et al., The Protein Folding Problem and Tertiary Structure, pp. 14–16, 1994.*
Aston et al., "Antigenic Structure of Bovine Growth Hormone: location of a Growth Enhancing Region," *Molecular Immunology*, 28:41–50, 1991.
Lehrman, S.R., et al., "Identification and characterization of an antiisoaspartic acid monoclonal antibody," *J. Protein Chem.* 11(6), 657–63, 1992.
Brems et al., "Helical formation in isolated fragments of bovine growth hormone;" Biochemistry 26(24), 774–8, 1987.

* cited by examiner

*Primary Examiner*—Yvonne Eyler
*Assistant Examiner*—Michael T Brannock
(74) *Attorney, Agent, or Firm*—Clark & Elbing LLP; Kristina Bieker-Brady

(57) ABSTRACT

A peptide construct including all or part of the sequence between positions 104 and 113 of growth hormone GH, or a homologous sequence cross-reactive therewith, is disclosed. The peptide fragment is covalently bonded to a transporter peptide and/or an adjuvant, and is capable of having an in vivo potentiating effect on the biological activity of said growth hormone.

9 Claims, No Drawings

BIOLOGICALLY ACTIVE AND PARTICULARLY PEPTIDE MOLECULES HAVING A POTENTIATING EFFECT ON GROWTH HORMONE BIOLOGICAL ACTIVITY

BACKGROUND OF THE INVENTION

1. Field of the Invention

The present invention relates to an active biological molecule of the peptide type which when it is linked covalently to certain transporter peptides and/or certain adjuvants is capable of inducing in vivo a potentiating effect on the biological activity of growth hormone GH.

2. Description of the Related Art

The potentiation of the biological activity, more particularly of the somatogenic activity, of GH by antibodies was first observed by Holder et al. (1980), who based their studies on the measurement of incorporation of radioactive sulfates into costal cartilage as well as on the weight gain induced by GH in Snell type dwarf mice.

Three studies based on the same parameters performed by Holder et al. (1985) and Aston et al. (1986 and 1987) showed that the majority of the antibodies studied had a potentiating effect on the biological action of GH. The work of Wallis et al. (1987) confirmed the phenomenon of enhancement of the somatogenic activity of bovine growth hormone by anti-GH antibodies. These latter based their studies on the measurement of the IGF-1 (insulin growth factor) plasma level and the weight gain of hypophysectomized rats of the Wistar strain.

In particular, the European patent application EP 284 406 (COOPERS ANIMAL HEALTH LTD.) described a peptide having a primary structure homology with a continuous sequence of amino acid residues of the growth hormone in the region extending from positions 35 to 53 or peptides with cross-reactivity, said peptide being usable in an antigenic composition to potentiate the effects of growth hormone in a vertebrate. The experiments described by Ashton et al. consist of an in vivo administration of antibodies, either in the form of sera when the latter are obtained from sheep, or in the form of monoclonal antibodies and this passive administration of antibodies directed against the peptide or directed against native natural growth hormone, complexed with said hormone, increases the biological activity of the latter. It has not been demonstrated that the peptide 35–53 of growth hormone could be used in the framework of active immunization.

Recent studies performed with potentiating antibodies would seem to indicate that if GH alone binds to hepatocytes, the GH-MAb complex or the complex formed between the hormone according to the invention and a monoclonal potentiating antibody would bind preferentially to the sinusoidal cells (Kupffer cells) (Tans et al. (1994)). Thus, it might consequently be assumed that the synthesis of IGF-1 and IGF BP3 in the hepatocytes (Massart et al. (1993)) might also be enhanced by the action of said complexes at these sinusoidal cells.

It is described in the patent application EP 137 234 (THE WELLCOME FOUNDATION LIMITED) that certain antibodies to growth hormone are capable of potentiating the activity of the latter whereas it is known that, usually, such antibodies have a tendency to antagonize its action, at least in vivo. Such antibodies may in addition be produced in situ by the "vaccination" of the host animal with a specific fragment of growth hormone, such that a class of polyclonal antibodies of restricted specificity is created which might potentiate the activity of the endogenous hormone.

BRIEF SUMMARY OF THE INVENTION

In the present invention it is shown that certain sequences of growth hormone linked to a carrier molecule and/or an adjuvant are capable of potentiating the activity of said hormone in a vertebrate. The discovery of the peptide fragment of the present invention is the result of research based initially on the selection of monoclonal antibodies (MAb) of the IgG class, whose reactivities towards growth hormone, in particular bovine growth hormone, appeared to be the highest. After purification of said MAb, four types were selected. The effect of these latter on the plasma IGF-1 response induced by a single injection of bGH into the immature hypophysectomized rat was assayed by Massart et al. (1993). Finally, it was possible to identify an epitope recognized by a potentiating antibody designated 2H4, this antibody being capable of specifically recognizing a peptide sequence situated in the α-helix No. 3 of native growth hormone.

Every reference to the primary, secondary or tertiary structure of GH refers to that described in Scanes C.G. et al. (1995).

The objective of the present invention is to provide a means for potentiating growth hormone GH more effectively and more durably than those of the prior art. In particular, the present invention provides a peptide or hapten capable of inducing in vivo a potentiating effect of the biological activity of this hormone when it is covalently linked to a transporter peptide and/or an adjuvant.

Such an effect may be the result of active immunization of the vaccination type, in which the administration of the hapten induces, in particular, the production of specific antibodies in vivo.

DETAILED DESCRIPTION OF THE INVENTION

The present invention thus relates to a peptide construction comprising all or part of the sequence extending from position 103 to position 114 of the growth hormone GH or of a homologous peptide of said sequence provided that it exhibits an immunological cross-reactivity with said sequence, this peptide fragment being linked covalently to a transporter peptide and/or an adjuvant and being capable of inducing in vivo a potentiating effect on the biological activity of said growth hormone.

The precise identification of this GH sequence or "GH peptide" resulted from the analysis of a certain number of anti-GH monoclonal antibodies, responsible for a potentiating effect on the administration of the antibody-GH complex. This peptide fragment, the peptide sequence of which derived from GH may also be considered as a hapten-type molecule, is recognized by the antibody 2H4. Moreover, among the antibodies having the highest potentiating effects it may be noted that the affinity of 2H4 for GH is low compared with those of other antibodies.

According to a preferred peptide construction of the invention, said sequence of growth hormone GH is comprised in the following sequence:

GTSDRVYEKL SEQ ID NO:1.

Even more preferably, said sequence of the GH is selected from the following sequences:

TSDRVYEKL SEQ ID NO:2;
GTSDRVYEK SEQ ID NO:3;

SDRVYEKL SEQ ID NO:4;

TSDRVYEK SEQ ID NO:5; or

GTSDRVYE SEQ ID NO:6.

These five peptides correspond to the regions 105–113, 10–112, 106–113, 105–112, 104–111, respectively, of the growth hormone GH as published in Scanes et al. (1995) and may be obtained by the standard procedures of peptide synthesis.

Since a hapten is, by definition, non-immunogenic, the peptide of the invention is coupled covalently to a transporter. As examples, such transporters may advantageously be peptide sequences derived from ovalbumin, KLH (keyhole limpet hemocyanin) or albumin and more particularly the following peptides:

323–339 of ovalbumin

378–398 or 379–398 or 378–397 or 378–396 or 378–395 of the peptide CS.T3 described by Sinigaglia et al., 45–60 of protein 1A of the respiratory syncitial virus 120–140 of the protein enveloping the genomic RNA of the hepatitis B virus.

These sequences are coupled covalently to the carboxyl or amino terminal of the "GH peptide".

The peptide fragment of the invention may be linked covalently to an adjuvant of the N-acetyl-muramyl (MAP) type, linked to a peptide like MDP or its derivatives.

According to a preferred embodiment of the peptide fragment according to the invention, the adjuvant is the muramyl-dipeptide (MDP) or one of its derivatives such as MDP-lysine, Lys (NH$_2$)—D—isoGlu—L—Ala—NMc—Nur.

The MDP derivative is then coupled covalently to the carboxyl end of the peptide consisting of the "GH peptide" and the transporter, approximately similar to that described in EP 89290.

The peptide fragment according to the invention may also be linked to a sequence known or presumed to be T-dependent with or without MDP or its derivatives or alternatively linked or incorporated into liposomes. It may also be administered in aqueous or oily media, by the oral route, in the form of subcutaneous, intramuscular or transmucosal injections, by "pellets" (biodegradable polymers containing the product) and by implantation of systems of dispersal by means of micropumps. Other adjuvants such as PAO alone or combined with lecithin (EP 445710), Zn(OH)$_2$ or HBW 538 (DRUGS.EXP.CLIN RES. 17 (9) 1991 445–450) combined with Al(OH)$_3$ may be linked covalently or not with the transporter GH peptide.

Finally, of course, several peptide fragments according to the invention may be bound to the same transporter molecule without the potentiating effect being affected.

The "GH peptides" or GH peptides coupled to transporter peptides may be synthesized chemically, by methods known to the specialist skilled in the art, as for example the Merrified procedure.

Such an approach which implies active immunization is a procedure possessing many advantages compared with the administration of antibodies. In fact, active immunization, like vaccination, makes possible a durable effect whereas the administration of antibodies has only a transient effect; in addition, the production of peptides is appreciably less expensive than that of antibodies or of native GH.

Also included in the framework of the present invention is a recombinant nucleic acid incorporating a nucleotide sequence coding for the "GH peptide" according to the invention, preferably coupled to the peptide transporter. Such a recombinant nucleic acid may be used:

either to transfect prokaryotic or eukaryotic cells and make them produce said peptides in vitro;

or as active ingredient of a medicine potentiating GH; the peptides are then produced in vivo by a mechanism similar to that described in WANG, B. et al. (1993).

The present invention also relates to an immunogenic composition containing a peptide fragment or a recombinant nucleic acid described above.

An adjuvant may be added to such a composition, whether coupled to the peptide as described above or not. A composition according to the invention may advantageously be used as feedstuffs additive to stimulate the growth and/or lactation of animals, in particular cattle, sheep, pigs and other vertebrates (fish, marsupials, humans . . . ). It may be intended for oral administration, for example in the form of feedstuffs additive, or for rectal, subcutaneous, intramuscular or transmucosal administration, or by "pellets" and micropump systems; in particular liposomes may be used as a vector in a composition incorporating the GH peptide, coupled or not to a transporter and an adjuvant.

For an effect designed to promote growth or lactation in animals, the composition is formulated such that the peptide of the invention is administered at a concentration of 0.01 µg to 10 µg per kg.

The peptides and the compositions of the invention may also be used in the case of humans in the manufacture of a medicine against growth disorders, whether the latter result from a deficit of endogenous growth hormone or from a disturbance of the metabolism of this latter. The formulations of these compositions would also be such as those defined above. Without being limiting, the examples and figures presented hereafter show the particularly advantageous effect of the peptide constructions of the invention, and particularly in comparison with other growth promoters.

DETAILED DESCRIPTION

1) Determination of the Sequence of the "GH Peptide"

In a preliminary step, it was necessary to select from among the different monoclonal antibodies directed against bGH those which exhibit a certain affinity for the latter. These latter seemed in fact to be those which would be the most likely to interfere positively or negatively with the biological activity of the hormone.

In order to obtain these antibodies a rapid immunization procedure described by Holmdahl et al. (1985) and Mirza et al. (1987) enabling specific monoclonal antibodies to be obtained was used. The antigen used was bGH.

The antibodies obtained were characterized with respect to:

isotypy reactivity in RIA with bGH labelled with iodine 125 reactivity in ELISA (additivity titration, capture)

reactivities in WESTERN-BLOT

The antibodies were then purified from ascites by the procedure described in Bruck et al. (1982), and once the purification was completed, the solutions of antibodies obtained were subjected to mini-electrophoresis on a denaturing gel with SDS (PHAST SYSTEM). The purpose of this operation is to check the isolation of the immunoglobulins.

The capacity of the purified MAbs to form high concentrations of immune complexes with bGH in solution was determined by a method described in particular by Massart. This reactivity is measured by the capacity of the antibody to form a complex with I$^{125}$ labelled bGH under precipitation conditions in the presence of PEG (polyethylene glycol).

This has enabled an antibody, designated 2H4 and exhibiting the desired reactivity, to be selected and studied with respect to its affinity for bGH. The results of the physico-chemical characteristics of this antibody are presented in the thesis of S. Massart and in Table 1 below.

TABLE 1

| No. clone | Antibody status | Isotype | RIA (1) | RIA (2) | RIA (3) | React. Titr. | ELISA CAPT. | W.B. React. |
|---|---|---|---|---|---|---|---|---|
| 2H4 | S, A | IgG1 (A) | +++ | +++ | ++++ | 10.3 | 9.3 | ++ |

S: culture supernatant
A: ascites fluid
(A): Isotype which is determined on the diluted ascites fluid and not on the culture supernatant
++: average precipitation
+++: heavy precipitation
++++: very heavy precipitation React. Titr.: Titration of the anti-bGH MAb of the ascites fluids (represents the O.D. value observed ranging from 0.200 (1) to 2,000 (10)).
ELISA capt.: capture of biotinylated bGH with the aid of antibodies adsorbed on plastic (represents the number of antibody dilutions showing the observed maximal O.D.)
b) Mapping of the Epitope Recognized by the Antibody 2H4:

The work described above thus enabled the epitope of the MAb 2H4 to be defined by epitopic mapping studies performed in particular according to Beattie and Holder (1994).

A battery of octapeptides was synthesized and allowed to react with the monoclonal antibodies. The peptides which bind to the antibodies were identified by spectrometry. The molecular weight of the antibody-peptide complexes is markedly higher than that of the peptides alone.

Consequently, it was demonstrated that the antibody binding site was the peptide 104–113 of the structure of GH.

This region 104–113 is located in the α-helix No. 3 of GH, a region of GH very little studied owing to the fact that the peptides of this helix exhibit a low radioreceptor activity (Scanes et al., Ed. 1995). However, it is known that the peptides of this region exhibit significant growth promoting activity, the α-helix No. 3 is in addition the region of the second binding site of the GH binding protein (GHBP). In fact, for the GH to bind to its hepatic receptor, it is necessary that it constitutes a dimer with two GHBP in order to induce the growth promoting effect according to the model of Fuh (1992) (Science, 256, 1677–1678). In the absence of this dimerization of the GH or GHBP no antagonistic action is produced and thus no growth promoting effect is obtained. It may then be supposed that the potentiating antibody facilitates or modifies this GHBP binding at the binding site, which might explain the advantageous effect of this "GH peptide".

EXAMPLES

In vivo experiments performed in the context of the present invention were carried out on 19 batches of hypophysectomised female rats of the Wistar strain, each batch comprising 5 rats. These animals were hypophysectomized when 4 weeks old and then kept under observation for one week. During an additional week of observation, the animals were weighed and those having gained more than 5 grams after seven weeks were discarded. In fact, it was assumed that the hypophysectomy of these animals was incomplete. They are thus not suitable for use in the framework of the present experiments.

Each animal selected receives a T4 thyroid hormone and cortisone replacement treatment. These hormones are administered subcutaneously each day at 50 μg/100 g body weight in the case of cortisone and 1 μg/100 g body weight in the case of T4. Usually a slight weight gain is observed following the injection of these hormones. This hormone supplementation treatment is administered for one week during which the animals continue to be weighed daily. These animals are from then on suitable for use in a comparative evaluation of the somatogenic activity of bGH incubated with or without different peptide constructions having the sequence 104–113 or the sequence 35–53 in the case of the GH peptide described in EP 284406.

During this evaluation which was performed during 50 days an attempt was made to measure by means of the weight gain and the level of IGF-1, the enhancement of the hormonal activity of porcine GH administered in the form of a complex with antibodies directed against peptide 104–113 as compared with peptide 35–53 of GH.

Peptide 104–113 was made immunogenic by coupling to different carrier molecules of peptide origin to form the peptide constructions described hereafter and which were then injected into individuals, coupled or not to adjuvants of various origins, in particular peptides derived from MDP, mineral oils, products of bacterial origin or diverse hydroxides. This composition was injected in a form containing said peptide constructions at 0.01 μg to 10 μg of composition per kg (rat weight).

In parallel, control rats, also hypophysectomized, receive injections of porcine GH at 0.01 μg to 10 μg per kg, either in the presence of normal immunoglobulins (negative controls) or in the presence of antibodies directed against peptide 35–53 of GH (supposed positive controls).

The two immunogens (35–53-OVA and 35–53-SRIF) were described in the European patent application EP 284406 as being efficacious for the production of antibodies capable of increasing the activity of GH in hypophysectomized Wistar rats. In the present experiments the peptide 35–53 of GH was also made immunogenic by the same covalent type of coupling as in the case of the peptide 104–113.

The immunogens 104–113-OVA, 104–113-LysMDP, 104–113-SRIF, 104–113-SRIF-LysMDP were hence compared with immunogens having the same type of conjugates (transporter molecules or adjuvants) but in which the peptide 104–113 has been replaced by the peptide 35–53.

The methods used for the conjugation of OVA and SRIF may be those described in the patent application EP 284406. In addition, the coupling to LysMDP may be performed according to the method described by Carelli et al. in the European patent EP 89290.

The detection of the anti-peptide and anti-GH antibodies was also performed according to the method described in the European patent application EP 284406.

The subcutaneous injection was given on days D-1, D-15 and D40 and bleedings were performed on days D-1, D-7, D-21, D45 and a final bleeding on D-50.
Description of the Batches:
 Batch 1: PBS (negative control)
 Batch 2: CFA (complete Freund's adjuvant, 2nd negative control)

Batch 3: IFA (incomplete Freund's adjuvant, 3rd negative control)

| Batch 4: | PBS | + | 104–113 | conjugated to OVA |
|---|---|---|---|---|
| Batch 5: | ACF | + | 104–113 | conjugated to OVA |
| Batch 6: | PBS | + | 35–53 | conjugated to OVA |
| Batch 7: | ACF | + | 35–53 | conjugated to OVA |
| Batch 8: | PBS | + | 104–113 | conjugated to SRIF |
| Batch 9: | ACF | + | 104–113 | conjugated to SRIF |
| Batch 10: | PBS | + | 35–53 | conjugated to SRIF |
| Batch 11: | ACF | + | 35–53 | conjugated to SRIF |
| Batch 12: | PBS | + | 104–113 | conjugated to MDPLys |
| Batch 13: | PBS | + | 35–53 | conjugated to MDPLys |
| Batch 14: | PBS | + | 104–113 | conjugated to SRIF conjugated to MDPLys |
| Batch 15: | PBS | + | 35–53 | conjugated to SRIF conjugated to MDPLys |
| Batch 16: | IFA | + | 104–113 | conjugated to MDPLys |
| Batch 17: | IFA | + | 35–53 | conjugated to MDPLys |
| Batch 18: | IFA | + | 104–113 | conjugated to SRIF conjugated to MDPLys |
| Batch 19: | IFA | + | 35–53 | conjugated to SRIF conjugated to MDPLys |

The following comparisons were then made on the different batches:
the induction of potentiating antibodies according to the method described in Massart (1989) pages 27 and 34.
the induction of anti-peptide antibodies, as well as the level of anti-peptide antibodies recognizing native GH
the change in weight
the level of plasma IGF-1

At the end of the treatment, after weighing of the individuals in all of the batches, the animals were sacrificed by decapitation without anaesthesia for the determination of the IGF-I level, and the weight changes and the IGF-I responses of the different experimental groups were compared in the different batches For the determination of the IGF-I level, the blood from the main blood vessels is collected in glass tubes. After retraction of the clot (2 hours at 4° C.) the samples are centrifuged and the sera are stored at –20° C.

The IGF-1 is then extracted according to the method described by Renaville et al. (1993), page 444. The level of recovery of IGF-1 by this procedure is 93%; more than 99% of the binding proteins are eliminated. The IGF-1 thus extracted is then assayed by radioimmunassay by using the Rab 2 antiserum (Renaville et al. (1993)).

First it is possible to note the similarity which exists between the two types of results since there actually exists a close correlation between the weight gains and the IGF-1 responses.

In fact, at the dose of 100 µg/rat bGH induces mean IGF levels of 60 ng/ml. This value is eight times higher than the baseline levels in control hypophysectomized animals.

The results of this experiment show that the peptide constructions with the GH peptide induce an increase of hormone activity. This increase is reflected in the IGF-1 concentration obtained which is higher than that of animals injected with bGH alone.

The results of this experiment also show that a correlation exists between the level of circulating antibodies recognizing the native hormone (GH) and the weight gain of the immunized rats. In particular, the batches receiving the peptides either conjugated to OVA and injected in the presence of CFA as well as those coupled directly to MDPLys and injected in PBS stand out clearly from the other batches. OVA is thus a better transporter than SRIF, even when this latter is coupled in turn to MDPLys.

The direct coupling of the peptides to MDPLys gives good results when it is administered in PBS rather than in IFA. It should also be noted that in the batches receiving the peptide 35–53, batch 7 gives a better result than the batches 13 and 17 but not as good as the batches 5 and 12.

BIBLIOGRAPHY (1) Aston et al. "Potentiation of the somatogenic and lactogenic activity of human GH with Mab" (1986) J. Endocrinol. 110, 381–388.
(2) Aston et al. "Enhancement of the bovine GH activity with Mab" (1987) Mol. Immunol. 24: 143–150.
(3) Beattie et al. Mol. Endocrinol. (1994) 8: 1103–1110.
(4) Bruck et al. (1982) "The Step purification of mouse Mab from ascitic fluid by DEAE affigel blue chromatography" J. of 53, Immunological Methodology 313–316.
(5) Fuh et al. Science (1994), 256, 1677–1678.
(6) Holder et al. "Effects of GH, prolactin and thyroxine on body weight, somatomedin-like activity and in vivo sulphation of cartilage in hypopituitary Snell dwarf mice" (1980) J. Endocrinol. 85: 34–47.
(7) Holder et al. "Monoclonal antibody-mediated enhancement of GH activity in vivo" (1980) J. Endocrinol. 107: R9–12.
(8) Holmdahl et al. "A rapid and efficient immunization protocol for production of monoclonal antibodies reactive with autoantigens" (1985) J. Immunol. Meth. 83: 379–384.
(9) Maiter et al. (1989) Endocrinolog, 124, 2604–2611.
(10) Massart S, Thèse de Doctorat "Etude de l'influence in vivo de Mab anti-bGH sur l'activité somatogénique de l'hormone b-GH" (1989) Faculté des Sciences Agronomiques de Gembloux-Belgique.
(11) Massart et al. (1993) "Mab to bGH potentiate hormonal activity in vivo by enhancing GH binding to hepatic somatogenic receptors" J. Endocrinology 139 383–393.
(12) Mirza et al."A comparison of spleen and lymph node cells as fusion partners of the raising of Mab after different routes of immunization" (1987) J. Immunol. Meth. 105 : 235–243.
(13) Renaville et al. (1993) "Changes in the hypophysial gonadal axis during the onset of puberty in young bulls" J. of Reproduction and Fertility 99, 443–449.
(14) Scanes et al. "Growth Hormone Chemistry" (1995) Growth Hormone, Ed. Harvey S., Scanes C. G. & Daugahaday W. H., CRC Press, London, pp 1–25.
(15) Sinigaglia et al. (1988) Nature. vol. 336 778–780.
(16) Tans et al. (1994) "Uptake by rat liver of bGH free or bound to a Mab", Bio Cell 82, 45–49.
(17) Wallis et al. (1987) "Mab to bGH potentiate effects of the hormone on somatomedin-C levels and growth of hypophysectomized rats" Biochem. Biophys. Res. Comm. 149: 187–193.
(18) Wang et al. (1993) PNAS 90 4156–4160.

A peptide construct including all or part of the sequence between positions 104 and 113 of growth hormone GH, or a homologous sequence cross-reactive therewith, is disclosed. The peptide fragment is covalently bonded to a transporter peptide and/or an adjuvant, and is capable of having an in vivo potentiating effect on the biological activity of the growth hormone.

What is claimed is:

1. An isolated peptide consisting of
   (a) a first peptide consisting of a sequence selected from the following sequences of SEQ ID NO:1, SEQ ID NO:2, SEQ ID NO:3, SEQ ID NO:4, SEQ ID NO:5, and SEQ ID NO:6; and
   (b) a carrier peptide, an adjuvant, and/or an otherwise heterologous peptide, said first peptide being covalently linked to said carrier peptide, adjuvant, and/or heterologous peptide;
   said isolated peptide having a potentiating effect on the biological activity of growth hormone.

2. The isolated peptide according to claim 1 wherein the carrier peptide is selected from the peptides consisting of:
   peptide 323–339 of ovalbumin,
   peptide 378–398 or 379–398 or 378–397 or 378–396 or 378–395 of the peptide CS. T3,
   peptide 45–60 of the A1 protein of the respiratory syncitial virus, and
   peptide 120–140 of the protein enveloping the genomic RNA of the hepatitis B virus.

3. The isolated peptide according to claim 1, wherein the adjuvant is a muramyl-dipeptide.

4. A composition containing an isolated peptide according to claim 1 and at least one adjuvant.

5. The isolated peptide according to claim 1, wherein said carrier peptide is covalently linked to the carboxyl-terminus of said first peptide and the adjuvant is covalently linked to the carboxyl terminus of said carrier.

6. The isolated peptide according to claim 1, wherein the adjuvant is a muramyl-dipeptide-lysine MDP-lysine.

7. The isolated peptide according to claim 3 or 6, wherein the adjuvant is linked covalently to the carboxyl-terminus of the first peptide.

8. The isolated peptide according to claim 3 or 6, wherein the adjuvant is linked covalently to the carboxyl-terminus of the carrier peptide.

9. The isolated peptide according to claim 1 wherein the adjuvant is a derivative of a muramyl-dipeptide.

* * * * *

SEQUENCE LISTING

<160> NUMBER OF SEQ ID NOS: 6

<210> SEQ ID NO 1
<211> LENGTH: 10
<212> TYPE: PRT
<213> ORGANISM: Artificial Sequence
<220> FEATURE:
<223> OTHER INFORMATION: Synthetic

<400> SEQUENCE: 1

Gly Thr Ser Asp Arg Val Tyr Glu Lys Leu
 1               5                  10

<210> SEQ ID NO 2
<211> LENGTH: 9
<212> TYPE: PRT
<213> ORGANISM: Artificial Sequence
<220> FEATURE:
<223> OTHER INFORMATION: Synthetic

<400> SEQUENCE: 2

Thr Ser Asp Arg Val Tyr Glu Lys Leu
 1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic

<400> SEQUENCE: 3

Gly Thr Ser Asp Arg Val Tyr Glu Lys
 1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Ser Asp Arg Val Tyr Glu Lys Leu
 1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic

<400> SEQUENCE: 5

Thr Ser Asp Arg Val Tyr Glu Lys
 1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic

```
<400> SEQUENCE: 6

Gly Thr Ser Asp Arg Val Tyr Glu
1               5
```